United States Patent [19]
Fraini et al.

[11] Patent Number: 5,399,776
[45] Date of Patent: Mar. 21, 1995

[54] PURIFICATION OF ACETONE

[75] Inventors: Edward A. Fraini, Lake Jackson; George W. Tepera, Sweeny, both of Tex.

[73] Assignee: The Dow Chemical Company, Midland, Mich.

[21] Appl. No.: 158,093

[22] Filed: Nov. 24, 1993

[51] Int. Cl.⁶ ............................................. C07C 45/80
[52] U.S. Cl. ................................................... 568/411
[58] Field of Search .................................. 568/410, 411

[56]  References Cited

U.S. PATENT DOCUMENTS

| | | | |
|---|---|---|---|
| 2,204,956 | 6/1941 | Bresler et al. | 568/411 |
| 2,429,484 | 10/1945 | Peters | 568/411 |
| 2,552,513 | 5/1951 | Blanchard et al. | 568/410 |
| 2,597,497 | 5/1952 | Joris | 568/411 |
| 2,624,699 | 9/1951 | Joris | 568/411 |
| 3,547,783 | 12/1970 | Yamaguchi et al. | 568/411 |
| 3,668,256 | 6/1972 | Brundege | 568/410 |
| 3,898,287 | 8/1975 | Gloyer | 568/410 |
| 4,066,650 | 1/1978 | Egyud | 568/410 |
| 4,336,109 | 6/1982 | Hasaka et al. | 568/411 |
| 4,722,769 | 2/1988 | Chan et al. | 568/411 |

FOREIGN PATENT DOCUMENTS

| | | | |
|---|---|---|---|
| 645090 | 9/1964 | Belgium | 568/411 |
| 789528 | 7/1968 | Canada | 568/410 |

*Primary Examiner*—James H. Reamer

[57] ABSTRACT

The present invention includes a process for removing aldehydes from acetone having aldehyde impurities comprising contacting the acetone with a sufficient amount of at least one diamine compound to react with at least a portion of the aldehyde and heating the acetone in the presence of the diamine compound sufficiently to result in reaction of the diamine compound and aldehyde, thus reducing the amount of aldehyde in the acetone. It is preferred that the process is an improvement in a process for purifying crude acetone having aldehydes therein, by fractionally distilling the acetone in a multiple plate distillation, the improvement comprising adding to the acetone a sufficient amount of at least one diamine compound to react with at least a portion of the aldehydes.

13 Claims, No Drawings

PURIFICATION OF ACETONE

BACKGROUND OF THE INVENTION

This invention relates to purification of ketones.

Acetone is produced in a number of ways most of which result in an acetone having undesirable by-products. While the instant invention is applicable to purification of any crude acetone such as produced by fermentation of isopropanol. Crude acetone compositions produced in decomposition of cumene hydroperoxide to produce phenol is of particular interest.

Crude acetone generally contains aldehydic substances such as formaldehyde, propionaldehyde and acetaldehyde. When such substances are present, the acetone fails commonly used tests for purity such as the National Formulary (NF) acetone test using potassium permanganate.

A number of methods of purification of acetone are reported. For instance, Joris in U.S. Pat. No. 2,624,699 reports heating crude acetone with activated carbon, graphite, diatomaceous earth, asbestos, pumice, coke, magnesia and sulfonated phenol-formaldehyde anion exchange resins impregnated with an alkali metal hydroxide and separating the so-treated acetone from its impurities. In U.S. Pat. No. 2,597,497 Joris reports a combination of distillation and extraction. Brundege in U.S. Pat. No. 3,668,256 reports continuously distilling crude acetone in a single, multiple-plate distillation tower in which a dilute alkaline solution mixes with the down flowing liquid so that said liquid remains rich in acetone and no other liquid phase is formed. In that process crude acetone is fed into a column through a feed inlet located in the lower section of the column above the stream source and below the alkali feed inlet. The alkali mixes with the downflowing liquid in the column forming a single, acetone-rich liquid phase which contacts the upflowing vapors of acetone and aldehydes, converting the aldehydes to nonvolatile polymers which tend to settle in the bottom of the column with water and the spent alkali. These polymers, however, are an undesirable by-product. In addition, the alkali results in increased conversion of acetone to diacetone alcohol and mesityl oxide.

It would be desirable to purify acetone such that formation of diacetone alcohol and/or mesityl oxide is substantially reduced or avoided. Diacetone alcohol is observed to convert to mesityl oxide such that a concentration of diacetone alcohol in acetone plateaus and the remainder converts to mesityl alcohol.

SUMMARY OF THE INVENTION

The present invention includes a method for removing aldehydes from acetone having aldehyde impurities comprising contacting the acetone with a sufficient amount of at least one diamine compound to react with at least a portion of the aldehyde and heating the acetone in the presence of the diamine compound sufficiently to result in reaction of the diamine compound and aldehyde.

A preferred embodiment of the invention includes an improvement in a process for purifying crude acetone having aldehydes therein, by fractionally distilling the acetone in a multiple plate distillation column having a lower first tray and upper top tray, wherein the acetone is fed to the column at a feed point between the first and top trays and is separated into liquid and gas phases, and purified acetone is removed as overhead product from the top of the column the improvement comprising adding to the acetone a sufficient amount of at least one diamine compound to react with at least a portion of the aldehydes.

Thus, the invention includes a process for purifying crude acetone by distillation in a multiple plate distillation column having a lower first tray and upper top tray comprising steps of:
  (a) feeding the crude acetone into the column at an acetone feed point between the first and top trays of the column;
  (b) heating the acetone sufficiently to separate it into liquid and gas phases;
  (c) feeding a diamine compound into the column such that it contacts the acetone;
  (d) removing purified acetone from the column at a point above the acetone feed point.

The steps are preferably simultaneous rather than sequential, particularly steps (a) and (c) are preferably simultaneous.

The diamine compound advantageously reacts with the aldehydes to form compounds which have boiling points sufficiently lower than acetone that they can be removed from the acetone by distillation, preferably in the same column in which the diamine compound is added to the acetone. The diamine compounds are advantageously insufficiently basic to result in as much formation of diacetone alcohol and mesityl oxide from the acetone as is observed when the acetone is contacted with inorganic base (especially sodium hydroxide) under the same conditions. Preferably, formation of diacetone alcohol and mesityl oxide is avoided.

DETAILED DESCRIPTION OF THE INVENTION

The crude acetone is suitably produced in any process and suitably contains any impurities including aldehydic impurities. In the most preferred embodiment of the invention, the crude acetone is that produced by decomposition of cumene hydroperoxide to obtain phenol.

The crude acetone is contacted with a diamine compound or resin. The diamine compound is suitably any compound having at least two primary amine groups. The diamine compound is suitably any size such as an amine resin, for instance, a styrene/divinylbenzene/diethylene amine ion exchange resin such as that commercially available from The Dow Chemical Company under the trade designation DOWEX ™ MW A-1. Smaller amine compounds are, however, preferred because of difficulties in recovering and reusing resins from the reacted state. Preferred compounds are those represented by the formula:

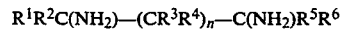

$$R^1R^2C(NH_2)\text{—}(CR^3R^4)_n\text{—}C(NH_2)R^5R^6$$

wherein each of $R^1$, $R^2$, $R^3$, $R^4$, $R^5$, and $R^6$ are independently H, alkyl groups, preferably of from 1 to about 5 carbon atoms, or alkaryl or aryl groups of from 6 to about 12 carbon atoms, or amine groups, more preferably H or alkyl groups of from 1 to about 3 carbon atom groups; and n is an integer of from 1 to about 6. The alkyl, alkaryl, and aryl groups are unsubstituted or inertly substituted. Exemplary diamine compounds include unsubstituted or inertly substituted tetraethylenepentamine (TEPA), 2,4-diamino-4-methylpentane (DAMP), 1,6 hexanediamine, 2,4-diamine-3,4-dimethyl-pentane; 2,4-diamino-3-ethyl-4-methyl pentane; 2,4-diamine-3-benzo-4-methyl pentane and the like. The term "inert substitution" is used to mean substitution which does not interfere undesirably with reaction of the diamine with aldehydes. Exemplary inert substitution includes alkyl and aryl groups, preferably of from 1 to about 3 carbon atoms for alkyl and of from 6 to about 12 carbon atoms for aryl groups, both more preferably insufficiently large or branched to result in steric hindrance of the amine groups. Of these, diamines capable of forming 5, 6 or 7 membered rings, that is having nitrogens separated by a chain of from 3 to 5 atoms, preferably carbon or nitrogen atoms are preferred. Of these diamines, those which react in at least about 30 minutes with aldehyde at contact temperatures or temperatures to which the acetone is exposed in distillation, e.g. about 40°–100° C., such as 1,4-diaminobutane, 1,5-diaminopentane, tetraethylenepentamine, and 2,4-diamino-4-methylpentane are preferred, with tetraethylenepentamine and 2,4-diamino-4-methylpentane more preferred.

Conditions of temperature, pressure, reaction time, apparatus and the like are not critical to the practice of the invention; however, the temperature is preferably sufficient for the diamine compound and the aldehydes to react at a desirable rate. It is believed that the reaction products are advantageously hexahydropyrimidines. Temperatures are advantageously at least about 40° C. but not above the boiling point of acetone at the desired pressure, or 56.5° C. at atmospheric pressure; preferably the temperature is at least about 50° C., more preferably at least about 55° C. When contact takes place outside a distillation apparatus or system, the temperature is conveniently less than about 56° C., more preferably less than about the boiling point of acetone at the preselected pressure. When contact takes place in a distillation apparatus or system, the temperature is preferably at least about the boiling point of acetone at the pressure encountered, at atmospheric pressure, at least about 56.5° C. Outside a distillation apparatus or system, the pressure is conveniently atmospheric, but optionally any pressure above or below atmospheric. While the amines are sufficiently reactive to remove aldehydes under the temperature and pressure conditions useful in commercially distilling acetone within the residence time in such a distillation column, at lower temperatures the removal reaction is slower. Determining the reaction time under preselected conditions is within the skill in the art by such methods as measuring remaining aldehydes.

The diamine compound is advantageously used in an amount sufficient to react with the aldehydes to be removed from the acetone. Those skilled in the art are able to determine this amount, for instance by determining the amount of aldehydes to be removed and using at least a stoichiometric amount of diamine compound. Preferably the diamine compound is used in slight molar excess, preferably at least about a 1.05 molar ratio of amine to aldehyde and more preferably about a 1.1 molar ratio of amine to aldehyde. For ease in removing excess diamine compound, and to avoid loss in reactions of diamine with acetone the amount of diamine is preferably less than or equal to about 1.1 molar ratio, more preferably about a 1.05 molar ratio.

The reaction product of the diamine compound and aldehyde is optionally and preferably removed from the acetone by means within the skill in the art such as by distillation (preferred), extraction, and the like.

In a preferred embodiment of the invention, contact of the diamine compound and acetone takes place in a distillation column during distillation of acetone. In the practice of that preferred embodiment, crude acetone is distilled in any multiplate (including multitray) distillation column wherein acetone is fed into the column at a feed point low in the column and pure acetone is withdrawn as an overhead product. The column preferably has a bottom portion not having trays, a middle portion having trays and an upper overhead portion above the trays not having trays. For instance and preferably, the process is as described in U.S. Pat. No. 3,668,256 (Brundege) but without addition of sodium hydroxide.

The acetone is suitably added to the distillation column at any position above the bottom tray of the tower, in the case of acetone containing water from which water is to be removed in the distillation, preferably at least about 5 trays above the bottom and preferably at least about 40 trays from the top to allow for purification in the distillation and to minimize product loss through the liquid phase removed from the bottom of the column. Most preferably, the acetone is added on about the eighth tray from the bottom of a distillation column having sufficient trays to separate the acetone from its impurities. As used herein the term "tray" refers to a physical tray in a column of any design such a sieve, bubblecap or valve tray.

The diamine compound is optionally fed to the column at any place from which it contacts the acetone. For instance, it is optionally mixed with the acetone before acetone is fed to the column, fed above the acetone in the headspace, or at a convenient tray above the acetone feed point high enough that sufficient contact takes place to reach the desired degree of reaction completion. Preferably the diamine compound mixed into the feed line at a point that the reaction reaches completion before the stream enters the column.

While conditions of temperature, pressure, reaction time, apparatus and the like are not critical to the practice of the invention, in the embodiment in which contact of the diamine compound and acetone occurs in a distillation tower, the temperature and pressure combination is a combination at which acetone distills. Especially when water is to be separated from the acetone, purer product is often obtained by operating with a slight vacuum on the overhead, preferably less than about 760 mm Hg (101 kPa), more preferably about 500 mm Hg (67 kPa) or less; preferably at least about 300 mm Hg (40 kPa), more preferably at least about 400 mm Hg (53 kPa). Those skilled in the art recognize that pressure will be higher down the column even when there is a slight vacuum on the top. Heat is provided by any means within the skill in the art, preferably by steam through the use of a steam jacket in a reboiler or a forced recirculation exchanger. When the diamine is added to the feed the heat is advantageously added with a heat exchanger within the skill in the art using steam or, less preferably for instance electrical heaters.

Practice of the invention advantageously results in less diacetone alcohol and/or mesityl oxide than does contact of the acetone with an amount of sodium hydroxide stoichiometrically equivalent to the amount of diamine compound; preferably the amount of diacetone alcohol and mesityl oxide is less than about 200 ppm by weight, most preferably formation of these compounds is substantially avoided, that is the amount of mesityl oxide and diacetone alcohol is less than 100 ppm (parts per million by weight).

The following examples are offered to illustrate but not to limit the invention. Examples of the invention (Ex.) are designated numerically while Comparative Samples (C. S.) are designated alphabetically and are not examples of the invention. All ratios, parts, and percentages are by weight unless designated otherwise.

EXAMPLE 1

Use of Tetraethylenepentamine to Reduce Aldehyde Concentration in Acetone

A vessel is charged with 100 grams of acetone containing 46 ppm (parts per million) by weight formaldehyde and 430 ppm by weight acetaldehyde. A sample, 0.5 grams, of tetraethylenepentamine is added to the charge. The charge is heated to 55° C. for time intervals of 10 and 30 minutes; a sample is taken after each interval and cooled to ambient (25° C.). Each sample is analyzed for components of interest. After only 10 minutes, the aldehyde levels are reduced to 13.0 and 24.0 ppm for formaldehyde and acetaldehyde, respectively.

The diacetone alcohol level in the product is 0.0 weight percent and the mesityl oxide level is also 0.0 weight percent.

TABLE 1

| interval in minutes | concentration of formaldehyde (ppm) | concentration of acetaldehyde (ppm) | concentration of mesityl oxide (ppm) | concentration of diacetone alcohol (ppm) |
|---|---|---|---|---|
| 0 | 46 | 430 | 0 | 0 |
| 10 | 13 | 24 | 0 | 0 |
| 30 | 10 | 8 | 81 | 7 |

This example shows that a diamine is effective in reducing the concentration of aldehydes in acetone and that use of a diamine results in much less diacetone alcohol and mesityl oxide formation than is observed with sodium hydroxide. (See Comparative Sample B.).

EXAMPLE 2

Use of 2,4-Diamino-4-methylpentane to Reduce Aldehyde Concentration in Acetone

The procedure of Example 1 is repeated using 0.5 grams of 2,4-diamino-4-methylpentane in place of the tetraethylenepentamine. After only 10 minutes, the aldehyde levels are reduced to 0.0 and 8.0 for formaldehyde and acetaldehyde, respectively. The diacetone alcohol level in the product is 0.0 weight percent and the mesityl oxide level is also 0.0.

TABLE 2

| interval in minutes | concentration of formaldehyde (ppm) | concentration of acetaldehyde (ppm) | concentration of mesityl oxide (ppm) | concentration of diacetone alcohol (ppm) |
|---|---|---|---|---|
| 0 | 46 | 430 | 0 | 0 |
| 10 | 0 | 8 | 0 | 0 |
| 30 | 0 | 5 | 76 | 9 |

This example shows that a diamine compound is effective in reducing the concentration of aldehydes in acetone and that it results in much less diacetone alcohol and mesityl oxide formation than is observed with sodium hydroxide in Comparative Sample B.

Comparative Sample A

Effect of Heat on Aldehydes in Acetone

A vessel is charged with 100 grams of acetone containing 107 ppm by weight formaldehyde and 577 ppm by weight acetaldehyde. The charge is heated to 55° C. for 30 minutes then cooled to ambient (25° C.). The charge is analyzed for the aldehydes, mesityl oxide and diacetone alcohol. No reduction in the aldehyde levels is detected; the diacetone alcohol level in the product is 2.0 ppm, and the mesityl oxide level is 42 ppm.

This sample is not an example of the invention, but rather is a control showing the effect of heat alone in the absence of the diamine compound on acetone. This sample demonstrates that the effects observed in Examples 1 and 2 are the result of the diamine compounds rather than heat.

Comparative Sample B

Use of Sodium Hydroxide to Reduce Aldehyde Concentration in Acetone

A vessel is charged with 100 grams of acetone containing 107 ppm by weight formaldehyde and 577 ppm by weight acetaldehyde. To the charge, 0.5 grams of caustic (sodium hydroxide) is added. The charge is heated to 55° C. for 30 minutes then cooled to ambient (25° C.). Analysis shows: aldehyde levels are reduced to 0.0 and 6.0 for formaldehyde and acetaldehyde, respectively. The diacetone alcohol level in the product is 5.8 weight percent, and the mesityl oxide level is 99 ppm.

TABLE 3

| interval in minutes | concentration of formaldehyde (ppm) | concentration of acetaldehyde (ppm) | concentration of mesityl oxide (ppm) | concentration of diacetone alcohol (ppm) |
|---|---|---|---|---|
| 0 | 107 | 577 | 5 | 37 |
| 10 | 37 | 326 | 4 | 513 |
| 30 | 0 | 6 | 99 | $5.8 \times 10^{+4}$ |

This is a comparative sample, not an example of the invention, and shows that use of sodium hydroxide in place of the diamine compounds results in lowering of the aldehyde concentrations accompanied by formation of diacetone alcohol and mesityl oxide. Because diacetone alcohol converts to mesityl oxide over time, the combined amounts of diacetone alcohol and mesityl oxide are the amounts most meaningfully compared. These combined amounts are much higher in Comparative Sample B than in the Examples of the invention.

We claim:

1. A process for removing aldehyde from acetone containing aldehyde impurities comprising contacting, the acetone with an amount of at least one diamine compound sufficient to react with at least a portion of the aldehyde and heating the acetone and diamine compound sufficiently to result in reaction of the diamine compound and aldehyde.

2. The process of claim 1 wherein the diamine compound is represented by the formula:

wherein each of $R^1$, $R^2$, $R^3$, $R^4$, $R^5$, and $R^6$ are independently H, alkyl groups, preferably of from 1 to about 5 carbon atoms, or alkaryl or aryl groups of from 6 to about 12 carbon atoms, or amine groups; and n is an integer of from 1 to about 6.

3. The process of claim 2 wherein each of $R^1$, $R^2$, $R^3$, $R^4$, $R^5$, and $R^6$ are independently H or alkyl groups of from 1 to about 3 carbon atoms.

4. The process of claim 1 wherein the diamine compound is an unsubstituted or inertly substituted tetraethylenepentamine (TEPA), 2,4-diamino-4-methylpentane (DAMP), 1,6 hexanediamine, 2,4-diamine-3,4-dimethyl-pentane; 2,4-diamino-3-ethyl-4-methyl pentane; 2,4-diamine-3-benzo-4-methyl pentane or mixture thereof.

5. The process of claim 1 wherein the contacting takes place outside a distillation apparatus or system, and the temperature is less than about 56° C.

6. The process of claim 1 wherein the contacting takes place in a distillation apparatus or system, the and temperature is at least about the boiling point of acetone.

7. The process of claim 1 wherein the diamine compound is used in at least about a 1 molar ratio of amine to aldehyde.

8. The process of claim 7 wherein the diamine compound is used in an amount of about a 1.1 molar ratio of amine to aldehyde.

9. The process of claim 1 wherein the diamine compound is mixed with the acetone before acetone is fed into a distillation column, fed above the acetone in headspace, or on a tray above the acetone feed point.

10. The process of claim 1 wherein less combined diacetone alcohol and mesityl oxide is produced by contact with the diamine compound than would be produced by contact of the acetone with an weight of sodium hydroxide equal to the weight of diamine compound.

11. The process of claim 10 wherein the amount of diacetone alcohol and mesityl oxide is less than about 200 ppm by weight in the acetone after treatment with diamine.

12. The process of claim 11 wherein the amount of mesityl oxide and diacetone alcohol is less than 100 ppm.

13. An improvement in a process for purifying crude acetone having aldehyde impurities therein, by fractionally distilling the crude acetone in distillation column having a lower first tray and upper top tray, wherein the acetone is fed to the column at a feed point between the first and top trays and is separated into liquid and gas phases, and purified acetone is removed as overhead product from the top of the column the improvement comprising adding sufficient diamine to the acetone to reduce the levels of aldehyde therein.

* * * * *